(12) United States Patent
McMillian

(10) Patent No.: US 7,029,840 B2
(45) Date of Patent: Apr. 18, 2006

(54) METHOD FOR PRESERVATION OF CELLS AND NUCLEIC ACID TARGETS

(75) Inventor: Ray A. McMillian, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/225,065

(22) Filed: Aug. 20, 2002

(65) Prior Publication Data

US 2003/0113705 A1  Jun. 19, 2003

Related U.S. Application Data

(63) Continuation-in-part of application No. 09/712,899, filed on Nov. 15, 2000, now abandoned.

(51) Int. Cl.
*A01N 1/02* (2006.01)
*C12N 5/02* (2006.01)
*C12Q 1/68* (2006.01)

(52) U.S. Cl. ............... 435/2; 435/6; 435/374
(58) Field of Classification Search ......... 424/488; 435/6, 69, 91.1, 94, 183, 269, 270, 278, 2, 435/374; 536/23.1, 24.3, 25.3, 25.4
See application file for complete search history.

(56) References Cited

U.S. PATENT DOCUMENTS 5,733,774 A * 3/1998 Jin et al. ............... 435/260
5,939,259 A * 8/1999 Harvey et al. ............ 435/6
6,107,098 A * 8/2000 Kalinich ............... 436/74
6,287,820 B1 * 9/2001 Umansky et al. ......... 435/91.1
2002/0102570 A1   8/2002 Baker

FOREIGN PATENT DOCUMENTS

JP     4118557 A2 *  4/1992

OTHER PUBLICATIONS

Von Worthington (Ed.) , Worthington enzyme Manual—enzymes and related biochemicals 1993. Worthington Biochemicals Corporation, Freehold, N.J., 07728, p. 374.*
Milde, A. et al. 1999. International Journal of Legal Medicine,vol. 112, pp. 209-210.*
Van Warmerdam, L.J. C et al. 1995. Validated method for the determination of carboplatin in biological fluids by Zeeman atomic absorption spectrometry. Fresenius' journal of analytical chemistry, vol. 351, No. 8, pp. 777-781.*

* cited by examiner

*Primary Examiner*—Ralph Gitomer
*Assistant Examiner*—Kailash C. Srivastava
(74) *Attorney, Agent, or Firm*—Allan M. Kiang

(57) ABSTRACT

The present invention provides a method for preserving cells and nucleic acids in a sample by exposing the sample to a composition that causes an inhibitory affect on proteolytic agents and/or nucleic acid degradative agents in the sample. Such compositions that are useful in the method of the present invention include chelating agents such as sodium citrate, sodium borate, sodium fluoride and EDTA, that will bind trace metals necessary for proteolytic activity of proteolytic agents and/or nuclease activity of nuclease agents in a sample.

7 Claims, No Drawings

METHOD FOR PRESERVATION OF CELLS AND NUCLEIC ACID TARGETS

This application is a continuation-in-part of 09/712,899, filed 11/15/2000, now abandoned.

BACKGROUND OF THE INVENTION

The field of the present invention broadly relates to retaining nucleic acid integrity in order that such nucleic acid is amenable to certain diagnostic processes, such as hybridization and amplification. More specifically, the present invention relates to the use of compositions that cause an inhibitory affect on proteolytic agents and/or nucleic acid degradative agents.

Diagnostic processes that utilize nucleic acid molecules include nucleic acid probe hybridization to determine the presence and/or amount of a target nucleic acid, nucleic acid primer hybridization for nucleic acid amplification processes and enzymatic activity including nucleic acid extension, nicking and/or cleavage. Nucleic acid amplification processes such as strand displacement amplification (SDA), polymerase chain reaction (PCR), ligase chain reaction (LCR), nucleic acid sequence based amplification (NASBA), transcription mediated amplification (TMA) and others are used to create multiple copies of a particular nucleic acid sequence(s) of interest (target sequence) which is present in lesser copy number in a sample.

A known method for inactivating DNases and proteolytic enzymes is to heat a sample at 100° C. for fifteen minutes (see, for example, Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989). Other methods for inactivating proteolytic enzymes use chaotropic agents, such as guanidinium thiocyanate or sodium thiocyanate, to denature these enzymatic proteins (see, for example, U.S. Pat. No. 4,843,155, incorporated herein by reference). In addition to inactivating nucleases and proteolytic enzymes, chaotropic agents are also known to promote lysis of cell walls in a wide range of biological materials (U.S. Pat. No. 5,234,809, incorporated herein by reference). The use of chaotropic agents to promote inactivation of proteases or nucleases should thus be avoided when preservation of cell walls is also desired.

A more general description of a method for preserving nucleic acids is provided by PCT Publication WO 00/50640 to Exact Laboratories wherein the use of EDTA and EGTA as nuclease inhibitors in methods for extracting DNA from exfoliated human epithelial cells in stool samples is disclosed. Also, Kyoto Ikagaku Kenkyusho: KK own two Japanese patent disclosures relating to methods for preserving cells in urine. In JP 04118557 A2, the use of citric acid as a buffering agent in addition to EDTA as an antibacterial drug is disclosed, and JP 05249104 A2 discloses the use of sodium fluoride as a fluorine compound in addition to citric acid and EDTA. Sierra, Diagnostics in PCT Publication WO 99/29904 disclose the use of ethylenediaminetetraacetic acid (EDTA), ethylenebis (oxyethylenenitrilo) tetraacetic acid (EGTA), 1,2-bis (2-aminophenoxy) ethane-N,N,N',N'-tetraacetic acid (BAPTA), or salts thereof in conjunction with at least one of the "chelator enhancing components" lithium chloride, guanidine, sodium salicylate, sodium perchlorate or sodium thiocyanate. Lithium chloride, guanidine, and sodium thiocyanate are known chaotropes to those skilled in the art. Effective concentrations of chelating enhancing components range from about 0.1 M to about 2.0 M.

Many of these methods are time consuming, labor intensive and/or have cumbersome safety requirements associated therewith. Another problem with methods that utilize relatively severe processing steps or conditions is the loss of some target nucleic acid sequence. Despite the ability of nucleic acid amplification processes to make multiple copies of target sequence (amplicons) from very few original targets, amplification efficiency and detection ability are improved if there are greater numbers of original targets in the sample. The greater detection ability can be very important when processing particularly difficult to detect samples such as acid fast *Bacillus* (AFB) smear negative *Mycobacterium tuberculosis* samples.

Another common problem with samples to be subjected to a molecular diagnostic process is the stability of the sample over time. Stability of the sample becomes more important when samples are taken at one location, but are then transported to another location such as a centralized laboratory for molecular diagnostic processing.

For example, many clinically relevant organisms do not maintain their integrity in urine samples and vaginal and cervical swabs for more than about twenty-four (24) hours at room temperature. Thus, refrigeration of such samples during transport to centralized laboratories and/or during storage has become a necessity. One analyte that is commonly tested from urine samples and swabs and is notoriously unstable in samples stored at room temperature is *Neisseria gonorrhoeae*.

SUMMARY OF THE INVENTION

In order to address the problems associated with maintaining the integrity of target nucleic acid and maintaining the stability of a sample and thus, achieve the benefits of improved detection of target nucleic acid sequences, the present invention provides a method for preserving cells and nucleic acids in a sample by exposing the sample to a composition that causes an inhibitory affect on proteolytic agents and/or nucleic acid degradative agents in the sample. Such compositions that are useful in the method of the present invention include chelating agents such as sodium citrate, sodium borate, sodium fluoride, and EDTA, that will bind trace metals necessary for proteolytic activity of proteolytic agents and/or nuclease activity of nucleic acid degradative agents in a sample. These compositions lack effective concentrations of "chelator enhancing components" or chaotropic agents.

DETAILED DESCRIPTION OF THE INVENTION

As stated above, the present invention relates to a method for preserving cells and nucleic acids in a sample by exposing the sample to a composition that lacks effective concentrations of "chelating enhancers" or chaotropic agents but nevertheless causes an inhibitory affect on proteolytic agents and/or nuclease agents in the sample. In the method, the sample is exposed to such a composition prior to lysis of cells in the sample such that cells containing nucleic acid will remain stable in the sample.

The types of samples which may be subjected to the method of the present invention include virtually all human and veterinary clinical samples such as sputum samples, blood samples, urine samples, cerebrospinal fluid ("CSF") samples, vaginal and cervical swabs and others, environmental samples such as water, air and soil samples, and food samples. The samples which may be subjected to the method of the present invention are suspected of containing cells with a target nucleic acid sequence to be subjected to a diagnostic process which may include hybridization, such as direct probe hybridization or primer hybridization for initiation of an amplification process.

The proteolytic agents typically found in such samples include proteolytic enzymes, such as proteases including endopeptidases such as renin, exopeptidases such as trypsin and chymotrypsin, and cathepsins. When present in a sample, proteolytic agents will cause degradation of cell walls, thus releasing nucleic acid, including any target nucleic acid for diagnosis. Such released nucleic acid is then subject to the actions of other agents that adversely affect diagnostic processes, including degradative enzymes, such as DNases and RNases, and substances that inhibit nucleic acid hybridization and/or amplification processes, such as porphyrin compounds derived from heme and hematin, serum enzymes such as aprotinin, leupeptin PMSF and pepstatin, and urea. The exposure of nucleic acid, particularly a target nucleic acid, to such agents adversely affects any diagnostic process to be performed with the nucleic acid. Thus, prevention of contact of the nucleic acid and such agents by inhibiting the premature lysis of cell walls allows for the maintenance of a stable sample for a longer period before a diagnostic process may be performed on the sample.

The method of the present invention involves the exposure of the sample to a composition that lacks effective concentrations of chelating enhancers or chaotropic agents and causes an inhibition of proteolytic agents and/or nucleic acid degradative agents in the sample. This exposure may occur at any time prior to the lysis of cells to release target nucleic acid. The exposure results in a reaction mixture containing the sample of cells and a composition that binds at least one co-factor necessary for activity of a proteolytic agent and/or a nucleic acid degradative agent Many such compositions are useful in the method of the present invention. Examples of such useful compositions include chelating agents such as sodium citrate, sodium borate, sodium fluoride and EDTA. Such chelating agents bind trace metals necessary for proteolytic activity of proteolytic agents in a sample. Thus, the proteolytic agents can not act as efficiently, or at all, to degrade cell walls. This allows the cell walls to remain intact, and the integrity of nucleic acid molecules within the cells is maintained, because such nucleic acid molecules are not exposed to agents that cause their degradation.

The compositions that cause the inhibition of proteolytic agents may be used in any form or state. For example, such compositions may be exposed to a sample as a liquid or as a solid in a dry granular form, a compressed tablet, a dissolvable capsule containing the composition or in a permeable vehicle such as a sack containing the composition. Also, the composition, in any form, may be added to a container holding the sample or incorporated in the container to which the sample is added.

The concentrations of such compositions that are useful for the methods of the present invention range from about 2.5 mM to about 350 mM, with a preferred range of about 5 mM to about 100 mM. The temperatures at which the methods of the present invention are effective range from about 5° C. to about 60° C.

Other compositions useful in the methods of the present invention can be identified by one of ordinary skill in the art with a reasonable expectation of success by performing routine screening assays directed towards the optimal characteristics of such compositions, e.g., causing the inhibition of proteolytic agents.

The Examples set forth herein provide a simple, straightforward, routine screening assay by which one of ordinary skill in the art can quickly determine whether a particular composition will be likely to be useful in the methods of the present invention.

When the composition and the sample are exposed to one another, trace metals, such as magnesium, calcium, zinc and manganese that are necessary co-factors for proteolytic agents, such as proteolytic enzymes, and nucleic acid degradative enzymes, such as DNases and RNases, are bound by the composition. In such a bound state, the trace metals are not available for their co-factor function. Thus, the degradative action of proteolytic agents on cell walls, and nucleic acid degradative enzymes on nucleic acids is inhibited.

The amount of time for exposure of the composition and the sample to one another for the method of the present invention to be effective is generally minimal, without any maximum time. The binding of trace metals begins almost immediately upon exposure of the composition and the sample to one another, and such binding does not diminish appreciably over time. As a general rule, the exposure of composition and sample to one another should not be less than about thirty (30) minutes for the method of the present invention to be effective.

Optionally, following such exposure, the composition and sample may be separated. Such separation may be conducted by a variety of means such as centrifugation, filtering, or if a permeable vehicle is used, then the permeable vehicle can be physically removed from the sample or the treated sample can simply be removed by pipetting.

A variety of processes are currently used to prepare target nucleic acids in samples for hybridization or amplification. For example, sputum samples that are processed to amplify mycobacterial nucleic acid sequences are typically subjected to a NALC/NaOH process. Similarly, other types of clinical samples are subjected to other well-known standard processes, for example, centrifugation for large volume samples such as blood and urine. The method of the present invention may be used before, as part of, or after those standard processes.

In addition to utility of the method of the present invention for preserving cell wall integrity and nucleic acid integrity, the method also stabilizes the sample for transport at room temperature. The inhibition of proteolytic agents and/or nucleic acid degradative agents resulting from the method of the present invention permits room temperature storage and transport of the sample over time periods greater than those presently available using traditional sample preservation methods. For example, using mixed bed ion exchange resins, such as those disclosed in European Patent Application Publication No. 0915171A2, permit room temperature storage of urine sample for as long as four days, whereas the method of the present invention as shown in the Examples below, permits room temperature storage of urine samples for at least fourteen (14) days.

The following examples illustrate specific embodiments of the invention described herein. As would be apparent to skilled artisans, various changes and modifications are possible and are contemplated within the scope of the invention described.

EXAMPLE 1

Protection of N. gonorrhoeae DNA from Degradation in Urine

The purpose of this Example was to determine if a method of the present invention eliminates the degradation of *N. gonorrhoeae* plasmid DNA in human urine.

Materials
BDProbeTeC™ ET *Neisseria gonorrhoeae* priming microwells (BD)
BDProbeTec™ ET *Neisseria gonorrhoeae* amplification microwells (BD)
BDProbeTeC™ ET *Neisseria gonorrhoeae* plasmid DNA (BD)
BDProbeTec™ ET instrument and instrument plates
BDProbeTec™ ET lysing heater
BDProbeTec™ ET priming and warming heater
BDProbeTeC™ ET pipettor and pipette tips
Sodium citrate, trisodium salt (Sigma)
Ethylenediaminetetraacetic acid, disodium salt "EDTA" (Sigma)
Negative pooled urine
Glycine HCl (Sigma)
Ferrosoferric oxide (Pea Ridge Iron Ore)
Dimethyl sulfoxide "DMSO" (Sigma)
Bicine (Sigma)
Glycerol (Sigma)
Potassium hydroxide "KOH" (Sigma)

Procedure:

Twenty-milliliter volumes of negative pooled urine were prepared with 10, 40, and 100 mM sodium citrate (final concentration); 10, 20, and 40 mM EDTA (final concentration); and without chemical additive. In addition, a 20-ml volume of negative pooled urine was heated for 30 minutes (heated-treated urine). The samples were incubated for 60 minutes at room temperature. After the incubation step, the samples were spiked with *N. gonorrhoeae* plasmid DNA (2500 DNA copies/ml). The samples were incubated for 60 minutes at room temperature. After the incubation step, two-ml volumes from each sample (eight replicates) were heated for 30 minutes at 114° C. to denature the DNA.

The heat-denatured DNA was isolated from the samples with paramagnetic particles in an acidic environment as described in U.S. Pat. No. 5,973,138. A 1-ml volume of the 8 replicates as described above was added to ferrosoferric oxide. A 100-ul volume of 6 M glycine HCl was added to each sample. The DNA-ferrosoferric oxide complexes were separated on a magnet and washed two times with a 900-ul volume of 1 mM glycine HCl to reduce the ionic strength and remove nonspecifically bound materials. The DNA was released from the ferrosoferric oxide with 480-ul volume of elution buffer (88.3 mM KOH, 177.8 mM bicine, 12.1% (v/v) glycerol, and 11.0% (v/v) DMSO [final concentration]).

Strand Displacement Amplification (SDA) was performed according to the manufacturer's instructions (BDProbeTec™ET *Chlamydia trachomatis* and *N. gonorrhoeae* Amplified DNA Assay Package Insert L-000203 [November 1999]). A 150-ul volume of each sample was added into a priming microwell. The priming microwell plate was incubated for 20 minutes at room temperature, after which the plate was incubated at 72.5° C. The amplification microwell plate was incubated at 54° C. After 10 minutes, a 100-ul volume from each priming microwell was added into the corresponding amplification microwell. The amplification microwell plate was place in a BD ProbeTec ET instrument. Data was reported as MOTA value (metric other than acceleration).

Results

The results are provided in the table below as the average amplification MOTA value (eight replicates) from each processed sample.

| Sample | Average MOTA Value |
| --- | --- |
| No additive | 26 |
| 10 mM sodium citrate | 6673 |
| 40 mM sodium citrate | 36684 |
| 100 mM sodium citrate | 24069 |
| 10 mM EDTA | 16103 |
| 20 mM EDTA | 16178 |
| 40 mM EDTA | 20007 |
| Heat-treated urine | 21967 |

Conclusions

The data of this Example indicate that sodium citrate at 10, 20, and 40 mM and EDTA at 10, 40, 100 mM protected *N. gonorrhoeae* plasmid DNA from degradation in human urine by endogenous nucleases. The data also show that heat-treated urine prevented the degradation of *N. gonorrhoeae* plasmid DNA.

EXAMPLE 2

Stability of Cells of N. gonorrhoeae in Urine with Sodium Citrate

The purpose of this Example was to determine the stability of intact cells of *N. gonorrhoeae* in human urine for a period of 14 days at room temperature.

Materials
Amplification reagents and equipment were the same as described in Example 1.
Sodium citrate (Sigma)
BSA/PBS (0.2% bovine serum albumin, 10 mM potassium phosphate buffer [pH 7.6], and
150 mM sodium chloride)
Negative pooled urine
CT/GC diluent (BD)
*N. gonorrhoeae* ATCC 19424
Dynac II centrifuge (BD)

Procedure

Eighty-milliliter volumes of negative pooled urine were prepared with and without 100 mM sodium citrate (final concentration). The samples were spiked with cells of *N. gonorrhoeae* a final concentration 2500 cells/ml. Each sample was incubated for 14 days at room temperature. At specific time points (day 0, 6, and 14), 2.0-ml volumes of each sample (eight replicates) was centrifuged at 2000×g for 30 minutes at room temperature. The supernate was decanted and the cell pellet was resuspended with a 2.0-ml volume of BSA/PBS, and then centrifuged at 2000×g for 30 minutes at room temperature. Again, the supernate was decanted and the cell pellet was resuspended with a 2.0-ml volume of CT/GC diluent. Each sample was heated for 30 minutes at 114° C. to lyse the cells. SDA was performed on the cell lysate as described in Example 1.

Results

The results are presented in the table below as the average amplification MOTA value (eight replicates) from each processed sample for 14 days.

| | Average MOTA Value | | | |
|---|---|---|---|---|
| Sample | Day 0 | Day 6 | Day 10 | Day 14 |
| No additive | 26683 | 9540 | 3424 | 4990 |
| 100 mM sodium citrate | 30200 | 25391 | 27522 | 20953 |

Conclusions

The data of this Example demonstrate that the addition of 100 mM sodium citrate to human urine inhibited the lysis of intact cells of N. gonorrhoeae and maintained their stability for minimum of 14 days at room temperature. In contrast, the cells were not stable in urine without sodium citrate and had the tendency to undergo lysis prior to centrifugation, as indicated by decreased MOTA values relative to day 0.

EXAMPLE 3

Stability of Cells of N. gonorrhoeae in Urine with other Chemical Additives

The purpose of this example was to determine whether or not other chemical additives can maintained the stability of intact cells of N. gonorrhoeae in human urine.

Materials
Amplification reagents and equipment were the same as described in Example 1.
BSA/PBS (0.2% bovine serum albumin, 10 mM potassium phosphate buffer [pH 7.6], and
150 mM sodium chloride)
Negative pooled urine
CT/GC diluent (BD)
N. gonorrhoeae ATCC 19424
Sodium citrate (Sigma)
Sucrose (Sigma)
Polyvinylpyrrolidone "PVP" [average molecular weight 40,000] (Sigma)
Magnesium chloride "$MgCl_2$,"
Sodium fluoride (Sigma)
Sodium formate (Sigma)
Sodium borate (Sigma)
Ethylenediaminetetraacetic acid, disodium salt "EDTA" (Sigma)
Ethylenebis(oxyethylenenitrilo) tetraacetic acid "EGTA" (Sigma)
Dynac II centrifuge (BD)

Procedure

Forty-milliliter volumes of negative urine was prepared with 100 mM sodium citrate (final concentration); 5, 10, and 15% (v/v) sucrose (final concentration); 5, 10, and 15% (v/v) PVP (final concentration); 5, 10, and 15 mM magnesium chloride (final concentration); 10 and 100 mM sodium fluoride (final concentration); 10 and 100 mM sodium formate (final concentration); 10 and 100 mM sodium borate (final concentration); 0.5 and 5 mM EDTA (final concentration); 0.5 and 5 mM EGTA (final concentration); and without chemical additive. The samples were spiked with cells of N. gonorrhoeae at a final concentration of 2500 cells/ml. Each sample was incubated for 6 days at room temperature. At specific time points (day 0 and 6), the samples were processed by centrifugation at 2000×g as described in Example 2. Each sample was heated for 30 minutes at 114° C. to lyse the cells. SDA was performed on the cell lysate as described in Example 1.

Results

The data are presented in the table below as the average amplification MOTA score (eight replicates) from each processed sample for 6 days.

| | Average MOTA Value | |
|---|---|---|
| Sample | Day 0 | Day 6 |
| No additive | 31886 | 2710 |
| 100 mM sodium citrate | 27310 | 26394 |
| 5% sucrose | 28427 | 501 |
| 10% sucrose | 29548 | 5555 |
| 15% sucrose | 27391 | 8497 |
| 5% PVP | 22234 | 4361 |
| 10% PVP | 26537 | 2404 |
| 15% PVP | 20306 | 163 |
| 5 mM $MgCl^2$ | 28072 | 1507 |
| 10 mM $MgCl^2$ | 27157 | 4547 |
| 15 mM $MgCl^2$ | 35926 | 4868 |
| 10 mM sodium fluoride | 32162 | 10894 |
| 100 mM sodium fluoride | 26385 | 24559 |
| 10 mM sodium formate | 34446 | 2211 |
| 100 mM sodium formate | 29357 | 2139 |
| 10 mM sodium borate | 26170 | 15464 |
| 100 mM sodium borate | 24607 | 28908 |
| 0.5 mM EDTA | 35950 | 650 |
| 5 mM EDTA | 32392 | 34445 |
| 0.5 mM EGTA | 32611 | 1150 |
| 5 mM EGTA | 34504 | 6931 |

Conclusions

The data of this Example indicate that the average amplification MOTA values for cells of N. gonorrhoeae with 100 mM sodium citrate, 100 mM sodium fluoride, 100 mM sodium borate, and 5 mM EDTA at day 0 and 6 were not significantly different. These data indicate that the stability of intact cells of N. gonorrhoeae was maintained in human urine with these chemical stabilizers. Furthermore, the results demonstrate that these chemical stabilizers performed in a similar manner as sodium citrate to prevent the lysis of intact cells of N. gonorrhoeae.

EXAMPLE 4

Stability of Cells of N. gonorrhoeae in Urine at Different Temperatures

The purpose of this Example was to determine whether or not stability of intact cells of N. gonorrhoeae can be maintained in urine with sodium citrate and the other chemical stabilizers as described in Example 3 for 6 days at 5, 25, 35, and 45° C.

Materials
Amplification reagents and equipment were the same as described in Example 1
BSA/PBS (0.2% bovine serum albumin, 10 mM phosphate buffer [pH 7.6], and 150 mM
sodium chloride)
Negative pooled urine
CT/GC diluent (BD)
N. gonorrhoeae ATCC 19424
Sodium citrate (Sigma)

Sodium fluoride (Sigma)
Sodium borate (Sigma)
Ethylenediaminetetraacetic acid "EDTA" (Sigma)
Dynac II centrifuge Procedure Seventy-milliliter volumes of negative pooled urine was prepared with 100 mM sodium citrate (final concentration); 100 mM sodium fluoride (final concentration); 100 mM sodium borate (final concentration); 5 mM EDTA (final concentration); and without chemical additive. The samples were spiked with cells of *N. gonorrhoeae* at a final concentration of 2500 cells/ml. Each sample was incubated for 6 days at 5, 25, 35, and 45° C. At specific time points (day 0 and 6), the samples were processed by centrifugation at 2000×g as described in Example 2. Each sample was heated for 30 minutes at 114° C. to lyse the cells. SDA was performed on the cell lysates as described in Example 1.

Results

The data are presented in the table below as the average MOTA value (eight replicates) from each sample for 6 days at 5, 25, 35, and 45° C.

Negative pooled urine
Ferrosoferric oxide (Pea Ridge Iron Ore)
Dimethyl sulfoxide "DMSO" (Sigma)
Bicine (Sigma)
Glycerol (Sigma)
Potassium hydroxide "KOH" (Sigma)

Procedure

Sixty-milliliter volumes of negative pooled urine were prepared with 100 mM sodium citrate (final concentration); 100 mM sodium fluoride (final concentration); 100 mM sodium borate (final concentration); 10 and 20 mM EDTA (final concentration); and no chemical additive. The samples were incubated for 60 minutes at room temperature. After the incubation step, the samples were spiked with *N. gonorrhoeae* plasmid DNA at a final concentration of 5000 DNA copies/ml. The samples were incubated for 3 days at

|  | Average MOTA Value | | | | | | | |
| --- | --- | --- | --- | --- | --- | --- | --- | --- |
|  | 5° C. | | 25° C. | | 35° C. | | 45° C. | |
| Sample | Day 0 | Day 6 | Day 0 | Day 6 | Day 0 | Day 6 | Day 0 | Day 6 |
| No additive | 58904 | 59755 | 62552 | 1383 | 55505 | 8129 | 81772 | 14725 |
| 100 mM sodium citrate | 56773 | 57701 | 59703 | 51791 | 54238 | 51468 | 59944 | 63623 |
| 100 mM sodium fluoride | 43807 | 59543 | 44945 | 47391 | 41608 | 47347 | 45741 | 48043 |
| 100 mM sodium borate | 41940 | 40325 | 49622 | 50745 | 60308 | 60296 | 63343 | 62283 |
| 5 mM EDTA | 50132 | 64610 | 54871 | 66009 | 57077 | 69291 | 62891 | 74667 |

Conclusion

The data of this Example indicate that there was no significant difference in the average MOTA values for intact cells of *N. gonorrhoeae* in human urine with 100 mM sodium citrate, 100 mM sodium fluoride, 100 mM sodium borate, and 5 mM EDTA for day 0 and 6 at 5, 25, 35, and 45° C. These results indicate that these chemical stabilizers gave good stabilization to the intact cells of *N. gonorrhoeae* in urine and prevented cell lysis for a minimum of 6 days. In contrast, the cells were not stable in urine without a chemical additive and had the tendency to undergo lysis prior to centrifugation within 6 days at temperatures 5, 25, 35, and 45° C., as indicated by decreased MOTA values relative to day 0.

room temperature. At specific time points (day 0 and 3), 2-ml volumes from each sample (eight replicates),were heated for 30 minutes at 114° C. to denature the DNA. The heat-denatured DNA was isolated from the samples with paramagnetic particles in an acidic environment as described in Example 1. SDA was performed on the isolated DNA as described in Example 1.

Results

The results are presented in the table below as the average MOTA value (eight replicates) from each sample after incubation for 3 days at room temperature.

EXAMPLE 5

Stability of *N. gonorrhoeae* DNA in Urine

The purpose of this Example was to determine whether *N. gonorrhoeae* plasmid DNA can be maintained in human urine with the chemical additives as described in Example 3 for 3 days at room temperature.

Materials
Amplification reagents and equipment were the described in Example 1
BDProbeTec ET Neisseria gonorrhoeae plasmid DNA (BD)
Ethylenediaminetetraacetic acid, disodium salt "EDTA" (Sigma)

|  | Average MOTA Value | |
| --- | --- | --- |
| Sample | Day 0 | Day 3 |
| No additive | 16339 | 20 |
| 100 mM sodium citrate | 26852 | 30978 |
| 100 mM sodium fluoride | 27811 | 42689 |
| 100 mM sodium borate | 23263 | 34089 |
| 10 mM EDTA | 32177 | 30445 |
| 20 mM EDTA | 34594 | 31366 |

Conclusions

The data of this Example demonstrate that 100 mM sodium citrate, 100 mM sodium fluoride, 100 mM sodium borate, 10 mM EDTA, and 20 mM EDTA protects *N. gonorrhoeae* plasmid DNA from degradation in urine from endogenous nucleases for a minimum of three days at room temperature. In the absence of a chemical additive in the urine, *N. gonorrhoeae* plasmid DNA was rapidly degraded.

EXAMPLE 6
Stability of Cells of *N. gonorrhoeae* in Urine with EDTA at Different Temperatures Over Time and Comparison of EDTA to a Commercially Available Urine Preservative The purpose of this Example was to determine whether or not stability of intact cells of *N. gonorrhoeae* can be maintained in urine with EDTA for 6 and 14 days at 5, 27, 33, 45 and 60° C. and to compare the effectiveness of EDTA versus a commercially available urine preservative, DNA/RNA Protect™ from Sierra Diagnostics, LLC.

Materials

Amplification reagents and equipment were the same as described in Example 1.
Ethylenediaminetetraacetic acid, dipotassium salt "EDTA" (Sigma)
DNA/RNA Protect (Sierra Diagnostics)
BSA/PBS (0.2 % bovine serum albumin, 10 mM potassium phosphate buffer [pH 7.6], and
150 mM sodium chloride)
Negative pooled urine
CT/GC diluent (BD)
*N. gonorrhoeae* ATCC 19424
Dynac II centrifuge (BD)

Procedure i) Potassium EDTA: Seventy-milliliter volumes of pooled negative urine were prepared with 10 mM potassium EDTA (final concentration). The samples were spiked with cells of *N. gonorrhoeae* at a final concentration of 2000 cells/ml. Each sample was incubated for 14 days at 5, 25, 33, 45, and 60° C. At specific time points (day 0, 6 and 14), the samples were processed by centrifugation at 2000×g as described in Example 3. Each sample was heated for 30 minutes at 114° C. to lyse the cells. SDA was performed on the cell lysates as described in Example 1.

ii) DNA/RNA Protect™: Seventy-milliliter volumes of pooled negative urine were prepared with 10% (v/v) DNA/RNA Protect™ (final concentration). The samples were spiked with cells of *N. gonorrhoeae* at a final concentration of 2000 cells/ml. Each sample was incubated for 14 days at 5, 25, 33, 45, and 60° C. At specific time points (day 0, 6 and 14), the samples were processed by centrifugation at 2000×g as described in Example 3. Each sample was heated for 30 minutes at 114° C. to lyse the cells. SDA was performed on the cell lysates as described in Example 1.

Results

The data are presented in the table below as the average MOTA value (eight replicates) from each sample for 6 and 14 days at 5, 27, 33, 45 and 60° C.

| | Average MOTA Value | | | | | | | | |
|---|---|---|---|---|---|---|---|---|---|
| | 5° C. | | | 27° C. | | | 33° C. | | |
| Sample | Day 0 | Day 6 | Day 14 | Day 0 | Day 6 | Day 14 | Day 0 | Day 6 | Day 14 |
| No additive | — | — | — | 25369 | 12 | 1135 | — | — | — |
| 10 mM EDTA | 26448 | 35234 | 36205 | 26448 | 31619 | 36994 | 26448 | 34252 | 38183 |
| DNA/RNA Protect ™ | 29367 | 32953 | 18968 | 29367 | 253 | 70 | 29367 | 241 | 112 |

| | Average MOTA Value | | | | | |
|---|---|---|---|---|---|---|
| | 45° C. | | | 60° C. | | |
| Sample | Day 0 | Day 6 | Day 14 | Day 0 | Day 6 | Day 14 |
| No additive | — | — | — | — | — | — |
| 10 mM EDTA | 26448 | 36132 | 41115 | 26448 | 32218 | 26259 |
| DNA/RNA Protect ™ | 29367 | 1039 | 1032 | 29367 | 17201 | 3509 |

Conclusion

The data of this Example demonstrate that the addition of 10 mM EDTA to human urine inhibited the lysis of intact cells of *N. gonorrhoeae* and maintained their stability for minimum of 14 days at 5, 27, 33, 45, and 60° C. In contrast, the cells were not stable in urine without EDTA at 27° C. and had the tendency to undergo lysis prior to centrifugation, as indicated by decreased MOTA values relative to day 0. Also, in the DNA/RNA Protect™-treated human urine, the cells were not stable by day 6 at 27and 33° C. and by day 14 at 5 and 60° C.

While the invention has been described with some specificity, modifications apparent to those with ordinary skill in the art may be made without departing from the scope of the invention. Various features of the invention are set forth in the following claims.

That which is claimed is:

1. A composition to preserve the integrity of nucleic acid in a urine sample comprising cells, said composition consisting essentially of at least one chelating compound, wherein:
   (a) when mixed with said urine sample, said chelating compound is at a concentration of about 5 mM to 20 mM;
   (b) said composition lacks effective concentrations of at least one chaotrope, wherein said effective concentration is from 0.1 to 2.0 M; and
   (c) said composition is at a temperature of about 50° C. to about 60° C.

2. The composition of claim 1, wherein the nucleic acid is deoxyribonucleic acid.

3. The composition of claim 1, wherein the nucleic acid is ribonucleic acid.

4. The composition of claim 1, wherein the chelating compound is selected from the group consisting of sodium citrate, sodium borate, sodium fluoride and EDTA.

5. A composition to preserve the integrity of nucleic acid in a urine sample comprising cells, said composition consisting essentially of at least one chelating compound, wherein:

(a) said chelating compound is selected from the group consisting of sodium citrate, sodium borate and sodium fluoride;
(b) said composition lacks effective concentrations of at least one chaotrope, wherein said effective concentration is from 0.1 to 2.0 M; and
(c) said composition is at a temperature of about 50 °C. to about 60° C.

6. The composition of claim 5, wherein the nucleic acid is deoxyribonucleic acid.

7. The composition of claim 5, wherein the nucleic acid is ribonucleic acid.

* * * * *